(12) United States Patent
Goel et al.

(10) Patent No.: US 11,861,073 B2
(45) Date of Patent: *Jan. 2, 2024

(54) GESTURE RECOGNITION

(71) Applicant: NIKE, Inc., Beaverton, OR (US)

(72) Inventors: Manan Goel, Portland, OR (US); Kate Cummings, Seattle, WA (US); Peter Laigar, Seattle, WA (US); David Switzer, Seattle, WA (US); Sebastian Imlay, Seattle, WA (US); Michael Lapinsky, Seattle, WA (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/973,899

(22) Filed: Oct. 26, 2022

(65) Prior Publication Data

US 2023/0048187 A1 Feb. 16, 2023

Related U.S. Application Data

(63) Continuation of application No. 17/564,392, filed on Dec. 29, 2021, now Pat. No. 11,513,610, which is a
(Continued)

(51) Int. Cl.
*G06F 3/01* (2006.01)
*G06F 1/3231* (2019.01)
(Continued)

(52) U.S. Cl.
CPC .............. *G06F 3/017* (2013.01); *G06F 1/163* (2013.01); *G06F 1/3231* (2013.01); *G06F 3/011* (2013.01);
(Continued)

(58) Field of Classification Search
CPC ....... G06K 9/00335–00355; G06F 2203/0331; G06F 3/03; G06F 3/0346; G06F 3/0304;
(Continued)

(56) References Cited

U.S. PATENT DOCUMENTS 5,774,357 A 6/1998 Hoffberg et al.
5,977,957 A 11/1999 Miller et al.
(Continued)

FOREIGN PATENT DOCUMENTS

CN 103170105 A 6/2013
JP 2002171316 A 6/2002
(Continued)

OTHER PUBLICATIONS

Nov. 5, 2014 (WO)—ISR—App. No. PCT/US2014/050044.
(Continued)

*Primary Examiner* — David S Posigian
(74) *Attorney, Agent, or Firm* — Banner & Witcoff, Ltd.

(57) ABSTRACT

An athletic performance monitoring system, including a gesture recognition processor configured to execute gesture recognition processes. Interaction with the athletic performance monitoring system may be based, at least in part, on gestures performed by a user, and may offer an alternative to making selections on the athletic performance monitoring system using physical buttons, which may be cumbersome and/or inconvenient to use while performing an athletic activity. Additionally, recognized gestures may be used to select one or more operational modes for the athletic performance monitoring system, such that a reduction in power consumption may be achieved.

20 Claims, 8 Drawing Sheets

Related U.S. Application Data continuation of application No. 14/453,997, filed on Aug. 7, 2014, now Pat. No. 11,243,611.

(60) Provisional application No. 61/863,249, filed on Aug. 7, 2013.

(51) Int. Cl.
*G06F 1/16* (2006.01)
*G06V 10/147* (2022.01)
*G06V 40/20* (2022.01)
*G09B 19/00* (2006.01)
*G16H 20/30* (2018.01)

(52) U.S. Cl.
CPC ............ *G06F 3/014* (2013.01); *G06V 10/147* (2022.01); *G06V 40/23* (2022.01); *G09B 19/0038* (2013.01); *G16H 20/30* (2018.01)

(58) Field of Classification Search
CPC .......... G06F 3/017; G06F 3/011; G06F 3/014; G06F 1/163; G06F 1/3231; G06F 11/3062; G06T 7/20–292; G06V 10/147; G06V 40/23; G06V 40/20–28; G09B 19/0038; G16H 20/30; Y02D 10/00; Y02D 30/50; H02M 1/0032–0035; G11C 2207/2227
See application file for complete search history.

(56) References Cited

U.S. PATENT DOCUMENTS

| | | |
|---|---|---|
| 6,115,482 A | 9/2000 | Sears et al. |
| 6,244,873 B1 | 6/2001 | Hill et al. |
| 6,249,606 B1 | 6/2001 | Kiraly et al. |
| 6,720,984 B1 | 4/2004 | Jorgensen et al. |
| 6,847,313 B2 | 1/2005 | Biswas |
| 7,565,295 B1 | 7/2009 | Hernandez-Rebollar |
| 7,633,527 B2 | 12/2009 | Pilu |
| 7,725,547 B2 | 5/2010 | Albertson et al. |
| 7,881,902 B1 | 2/2011 | Kahn et al. |
| 8,064,560 B2 | 11/2011 | Hunter et al. |
| 8,147,248 B2 | 4/2012 | Rimas-Ribikauskas et al. |
| 8,265,900 B2 | 9/2012 | Irlam et al. |
| 8,284,847 B2 | 10/2012 | Adermann |
| 8,320,578 B2 | 11/2012 | Kahn et al. |
| 8,406,085 B2 | 3/2013 | Sakita |
| 8,436,821 B1 | 5/2013 | Plichta et al. |
| 8,447,704 B2 | 5/2013 | Tan et al. |
| 8,638,190 B1 | 1/2014 | Want et al. |
| 8,747,336 B2 | 6/2014 | Tran |
| 8,760,392 B2 | 6/2014 | Lloyd et al. |
| 8,876,738 B1 | 11/2014 | Kahn et al. |
| 8,896,529 B2 | 11/2014 | Immonen et al. |
| 8,902,154 B1 | 12/2014 | Kahn et al. |
| 9,000,887 B2 | 4/2015 | Linsky et al. |
| 9,060,683 B2 | 6/2015 | Tran |
| 9,110,505 B2 | 8/2015 | Mastandrea, Jr. |
| 9,149,222 B1 | 10/2015 | Zets et al. |
| 9,314,666 B2 | 4/2016 | Canavan et al. |
| 9,335,790 B2 | 5/2016 | Stotler |
| 9,374,279 B2 | 6/2016 | Yuen et al. |
| 9,442,570 B2 | 9/2016 | Slonneger |
| 9,575,544 B2 | 2/2017 | Bryger et al. |
| 9,600,169 B2 | 3/2017 | de Sa et al. |
| 9,603,524 B2 | 3/2017 | Park et al. |
| 9,646,481 B2 | 5/2017 | Messenger et al. |
| 9,652,135 B2 | 5/2017 | Seo et al. |
| 9,689,887 B1 | 6/2017 | Srinivas et al. |
| 9,696,811 B2 | 7/2017 | Yang |
| 9,703,384 B2 | 7/2017 | Kita |
| 9,703,397 B2 | 7/2017 | Nasiri et al. |
| 9,724,562 B2 | 8/2017 | Bailly et al. |
| 9,734,304 B2 | 8/2017 | Blackadar et al. |
| 9,746,926 B2 | 8/2017 | Raffa et al. |
| 9,782,104 B2 | 10/2017 | MacEachern et al. |
| 9,885,734 B2 | 2/2018 | Liou et al. |
| 10,216,894 B2 | 2/2019 | Hong et al. |
| 10,416,740 B2 | 9/2019 | Singh et al. |
| 10,459,495 B2 | 10/2019 | Griffin |
| 10,545,558 B1 | 1/2020 | Douglas et al. |
| 10,575,760 B2 | 3/2020 | Houmanfar et al. |
| 2001/0015123 A1 | 8/2001 | Nishitani et al. |
| 2003/0138130 A1 | 7/2003 | Cohen et al. |
| 2004/0112151 A1 | 6/2004 | Maxwell et al. |
| 2005/0078172 A1 | 4/2005 | Harville et al. |
| 2005/0210419 A1 | 9/2005 | Kela et al. |
| 2005/0238201 A1 | 10/2005 | Shamaie |
| 2006/0028429 A1 | 2/2006 | Kanevsky et al. |
| 2007/0164856 A1 | 7/2007 | Egner et al. |
| 2008/0089587 A1 | 4/2008 | Kim et al. |
| 2008/0129694 A1 | 6/2008 | Haven |
| 2008/0140338 A1 | 6/2008 | No et al. |
| 2008/0152202 A1 | 6/2008 | Moise et al. |
| 2008/0163130 A1 | 7/2008 | Westerman |
| 2008/0174547 A1 | 7/2008 | Kanevsky et al. |
| 2008/0178126 A1 | 7/2008 | Beeck et al. |
| 2009/0184849 A1 | 7/2009 | Nasiri et al. |
| 2009/0217211 A1 | 8/2009 | Hildreth et al. |
| 2009/0228841 A1 | 9/2009 | Hildreth |
| 2009/0234614 A1 | 9/2009 | Kahn et al. |
| 2009/0265671 A1 | 10/2009 | Sachs et al. |
| 2009/0271004 A1 | 10/2009 | Zecchin et al. |
| 2009/0319221 A1 | 12/2009 | Kahn et al. |
| 2010/0013944 A1 | 1/2010 | Venetsky et al. |
| 2010/0123605 A1 | 5/2010 | Wilson |
| 2010/0160014 A1 | 6/2010 | Galasso et al. |
| 2010/0210975 A1 | 8/2010 | Anthony, III et al. |
| 2010/0259285 A1 | 10/2010 | Koli et al. |
| 2010/0306716 A1 | 12/2010 | Perez |
| 2011/0037419 A1 | 2/2011 | Hoffman et al. |
| 2011/0054359 A1 | 3/2011 | Sazonov et al. |
| 2011/0066984 A1 | 3/2011 | Li |
| 2011/0081889 A1 | 4/2011 | Gao et al. |
| 2011/0096954 A1 | 4/2011 | Dahl |
| 2011/0112771 A1 | 5/2011 | French |
| 2011/0134251 A1 | 6/2011 | Kim et al. |
| 2011/0167391 A1 | 7/2011 | Momeyer et al. |
| 2011/0172743 A1 | 7/2011 | Davis et al. |
| 2011/0197161 A1 | 8/2011 | Mattingly et al. |
| 2011/0199292 A1 | 8/2011 | Kilbride |
| 2011/0214082 A1 | 9/2011 | Osterhout et al. |
| 2011/0254760 A1 | 10/2011 | Lloyd et al. |
| 2012/0005248 A1 | 1/2012 | Garudadri et al. |
| 2012/0007713 A1 | 1/2012 | Nasiri et al. |
| 2012/0016641 A1 | 1/2012 | Raffa et al. |
| 2012/0017232 A1 | 1/2012 | Hoffberg et al. |
| 2012/0029314 A1 | 2/2012 | Paquet et al. |
| 2012/0034888 A1 | 2/2012 | De Flaviis |
| 2012/0083705 A1 | 4/2012 | Yuen et al. |
| 2012/0093360 A1 | 4/2012 | Subramanian et al. |
| 2012/0094814 A1 | 4/2012 | Atkins et al. |
| 2012/0114181 A1 | 5/2012 | Borthwick et al. |
| 2012/0131513 A1 | 5/2012 | Ansell |
| 2012/0165074 A1 | 6/2012 | Soldan et al. |
| 2012/0200491 A1 | 8/2012 | Miller, IV |
| 2012/0200497 A1 | 8/2012 | Nasiri et al. |
| 2012/0206339 A1 | 8/2012 | Dahl |
| 2012/0220233 A1 | 8/2012 | Teague et al. |
| 2012/0253486 A1 | 10/2012 | Niemimaki |
| 2012/0259652 A1 | 10/2012 | Mallon et al. |
| 2012/0293404 A1 | 11/2012 | Federico et al. |
| 2012/0306745 A1 | 12/2012 | Moore et al. |
| 2012/0316406 A1 | 12/2012 | Rahman et al. |
| 2012/0319940 A1 | 12/2012 | Bress et al. |
| 2012/0323521 A1 | 12/2012 | De Foras et al. |
| 2013/0027341 A1 | 1/2013 | Mastandrea |
| 2013/0103856 A1 | 4/2013 | Dods et al. |
| 2013/0106684 A1 | 5/2013 | Weast et al. |
| 2013/0108994 A1 | 5/2013 | Srinivasa et al. |
| 2013/0114380 A1 | 5/2013 | Bryger et al. |
| 2013/0120282 A1 | 5/2013 | Kukulski |
| 2013/0142417 A1 | 6/2013 | Kutliroff et al. |

(56) References Cited

U.S. PATENT DOCUMENTS

| | | |
|---|---|---|
| 2013/0158686 A1 | 6/2013 | Zhang et al. |
| 2013/0165098 A1 | 6/2013 | Nakazawa et al. |
| 2013/0176258 A1 | 7/2013 | Dahl et al. |
| 2013/0190903 A1 | 7/2013 | Balakrishnan et al. |
| 2013/0191034 A1 | 7/2013 | Weast et al. |
| 2013/0194066 A1 | 8/2013 | Rahman et al. |
| 2013/0194193 A1 | 8/2013 | Kawalkar |
| 2013/0194287 A1 | 8/2013 | Nicholson et al. |
| 2013/0194966 A1 | 8/2013 | Wang et al. |
| 2013/0217979 A1 | 8/2013 | Blackadar et al. |
| 2013/0226039 A1 | 8/2013 | Shani et al. |
| 2013/0275794 A1 | 10/2013 | Annavaram et al. |
| 2014/0149060 A1 | 5/2014 | Meduna et al. |
| 2014/0201666 A1 | 7/2014 | Bedikian et al. |
| 2014/0215056 A1 | 7/2014 | Malakhova et al. |
| 2014/0225841 A1 | 8/2014 | Sultenfuss et al. |
| 2014/0236529 A1 | 8/2014 | Gyorfi |
| 2014/0267799 A1 | 9/2014 | Sadasivam et al. |
| 2014/0270375 A1 | 9/2014 | Canavan et al. |
| 2014/0278220 A1 | 9/2014 | Yuen |
| 2014/0278229 A1 | 9/2014 | Hong et al. |
| 2014/0288876 A1 | 9/2014 | Donaldson |
| 2014/0376876 A1 | 12/2014 | Bentley et al. |
| 2015/0119728 A1 | 4/2015 | Blackadar et al. |
| 2015/0220109 A1 | 8/2015 | von Badinski et al. |
| 2015/0346834 A1 | 12/2015 | Martinez Fernandez et al. |
| 2016/0065491 A1 | 3/2016 | Bentley et al. |
| 2016/0188181 A1 | 6/2016 | Smith |
| 2016/0301581 A1 | 10/2016 | Carter et al. |
| 2017/0056722 A1 | 3/2017 | Singh et al. |
| 2017/0285757 A1 | 10/2017 | Robertson et al. |
| 2017/0344859 A1 | 11/2017 | Mo |
| 2018/0120420 A1 | 5/2018 | McMahon et al. |
| 2018/0153430 A1 | 6/2018 | Ang et al. |
| 2019/0224528 A1 | 7/2019 | Omid-Zohoor et al. |

FOREIGN PATENT DOCUMENTS

| | | |
|---|---|---|
| JP | 2006288970 A | 10/2006 |
| JP | 2007006970 A | 1/2007 |
| JP | 2010539617 A | 12/2010 |
| JP | 2011512222 A | 4/2011 |
| JP | 2011200584 A | 10/2011 |
| JP | 2012024394 A | 2/2012 |
| WO | 2012171025 A1 | 12/2012 |
| WO | 2014193628 A1 | 12/2014 |

OTHER PUBLICATIONS

Fahad Moiz et al., A Comparative Study of Classification Methods for Gesture Recognition using a wristwatch device, 2009, IEEE 2011, Proceedings of International Joint Conference on Neural Networks, pp. 2479-2486 (Year: 2011).

Roman Amstutz et al., "Performance analysis of an HMM-based gesture recognition using a wristwatch device," 2009, IEEE Computer Society, pp. 303-309.

T. Marasovic and V. Papíc, "Accelerometer-based gesture classification using principal component analysis," SoftCOM 2011, 19th International Conference on Software, Telecommunications and Computer Networks, Split, 2011, pp. 1-5 (Year: 2011).

G. Raffa, Jinown Lee, L. Nachman and Junehwa Song, "Don't slow me down: Bringing energy efficiency to continuous gesture recognition," International Symposium on Wearable Computers (ISWC) 2010, Seoul, 2010, pp. 1-8, doi: 10.1109/ISWC.2010.5665872. (Year: 2010).

A.L. Wood, G.V. Merrett, S.R. Gunn, B.M. Al-Hashimi, N.R. Shadbolt and W. Hall, "Adaptive sampling in context-aware systems: A machine learning approach," IET Conference on Wireless Sensor Systems (WSS 2012), London, 2012, pp. 1-5, doi: 10.1049/cp.2012.0608. (Year: 2012).

French, Brian, et al., "Selective Sampling Strategies to Conserve Power in Context Aware Devices," 2007 IEEE, downloaded on Jan. 6, 2021, 4 pages.

GESTURE RECOGNITION

CROSS REFERENCE TO RELATED APPLICATIONS

This application is a continuation of and claims priority to U.S. patent application Ser. No. 17/564,392 filed Dec. 29, 2021, and entitled "Gesture Recognition," which is a continuation of U.S. patent application Ser. No. 14/453,997, now U.S. Pat. No. 11,243,611, filed on Aug. 7, 2014, and entitled "Gesture Recognition," which claims the benefit of and priority to U.S. Provisional Patent Application No. 61/863,249, filed on Aug. 7, 2013, and entitled "Gesture Recognition," the content of each of which is incorporated herein by reference in its entirety.

BACKGROUND

Modern technology has given rise to a wide variety of different electronic and/or communication devices that keep users in touch with one another, entertained, and informed. A wide variety of portable electronic devices are available for these purposes, such as: cellular telephones; personal digital assistants ("PDAs"); pagers; beepers; MP3 or other audio playback devices; radios; portable televisions, DVD players, or other video playing devices; watches; GPS systems; etc. Many people like to carry one or more of these types of devices with them when they exercise and/or participate in athletic events, for example, to keep them in contact with others (e.g., in case of inclement weather, injuries; or emergencies; to contact coaches or trainers; etc.), to keep them entertained, to provide information (time, direction, location, and the like).

Athletic performance monitoring systems also have benefited from recent advancements in electronic device and digital technology. Electronic performance monitoring devices allow for monitoring of many physical or physiological characteristics associated with exercise or other athletic performances, including, for example: speed and distance data, altitude data, GPS data, heart rate, pulse rate, blood pressure data, body temperature, etc. Specifically, these athletic performance monitoring systems have benefited from recent advancements in microprocessor design, allowing increasingly complex computations and processes to be executed by microprocessors of successively diminutive size. These modern microprocessors may be used for execution of activity recognition processes, such that a sport or activity that is being carried out by an athlete can be recognized, and information related to that sport or activity can be analyzed and/or stored. However, in some instances, interaction with these performance monitoring systems may be cumbersome, and require an athlete to make on-device selections using an array of buttons typical of a conventional computer system or portable electronic device. For an athlete performing an athletic activity, it may prove distracting, uncomfortable, or unfeasible to interact with a performance monitoring system, and make selections in relation to the functionality of the system in a conventional manner. Additionally, these systems are often powered by limited power sources, such as rechargeable batteries, such that a device may be worn by an athlete to allow for portable activity monitoring and recognition. As the computations carried out by athletic performance monitoring systems have become increasingly complex, the power consumption of the integral microprocessors carrying out the computations has increased significantly. Consequently, the usable time between battery recharges has decreased. Accordingly, there is a need for more efficient systems and methods for interacting with an athletic performance monitoring device, and for prolonging the battery life of athletic performance monitoring systems.

Aspects of this disclosure are directed towards novel systems and methods that address one or more of these deficiencies. Further aspects relate to minimizing other shortcomings in the art

SUMMARY

The following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

Aspects of the systems and methods described herein relate to non-transitory computer-readable media with computer-executable instructions for receiving acceleration data into a gesture recognition processor in a device. The device may be positioned on an appendage of a user, and operate according to a first operational mode. The received acceleration data may represent movement of an appendage of the user, and may be classified as a gesture. Upon classification, the device may be operated according to a second operational mode, wherein the second operational mode is selected based on the classified gesture.

In another aspect, this disclosure relates to an apparatus configured to be worn on an appendage of a user, including a sensor configured to capture acceleration data, a gesture recognition processor, and activity processor. The apparatus further includes a non-transitory computer-readable medium comprising computer-executable instructions for classifying captured acceleration data as a gesture, and selecting an operational mode for the activity processor based on the classified gesture.

In yet another aspect, this disclosure relates to non-transitory computer-readable media with computer-executable instructions that when executed by a processor is configured to receive motion data from a sensor on a device, identify or select a gesture from the data, and adjust an operational mode of the device based on the identified gesture.

This Summary is provided to introduce a selection of concepts in a simplified form that are further described below in the Detailed Description. The Summary is not intended to identify key features or essential features of the claimed subject matter, nor is it intended to be used to limit the scope of the claimed subject matter.

DETAILED DESCRIPTION

Aspects of this disclosure involve recognition of gestures performed by an athlete in order to invoke certain functions related to an athletic performance monitoring device. Gestures may be recognized from athletic data that includes, in addition to gesture information, athletic data representative of one or more athletic activities being performed by an athlete/user. The athletic data may be actively or passively sensed and/or stored in one or more non-transitory storage mediums, and used to generate an output, such as for example, calculated athletic attributes, feedback signals to provide guidance, and/or other information. These, and other aspects, will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
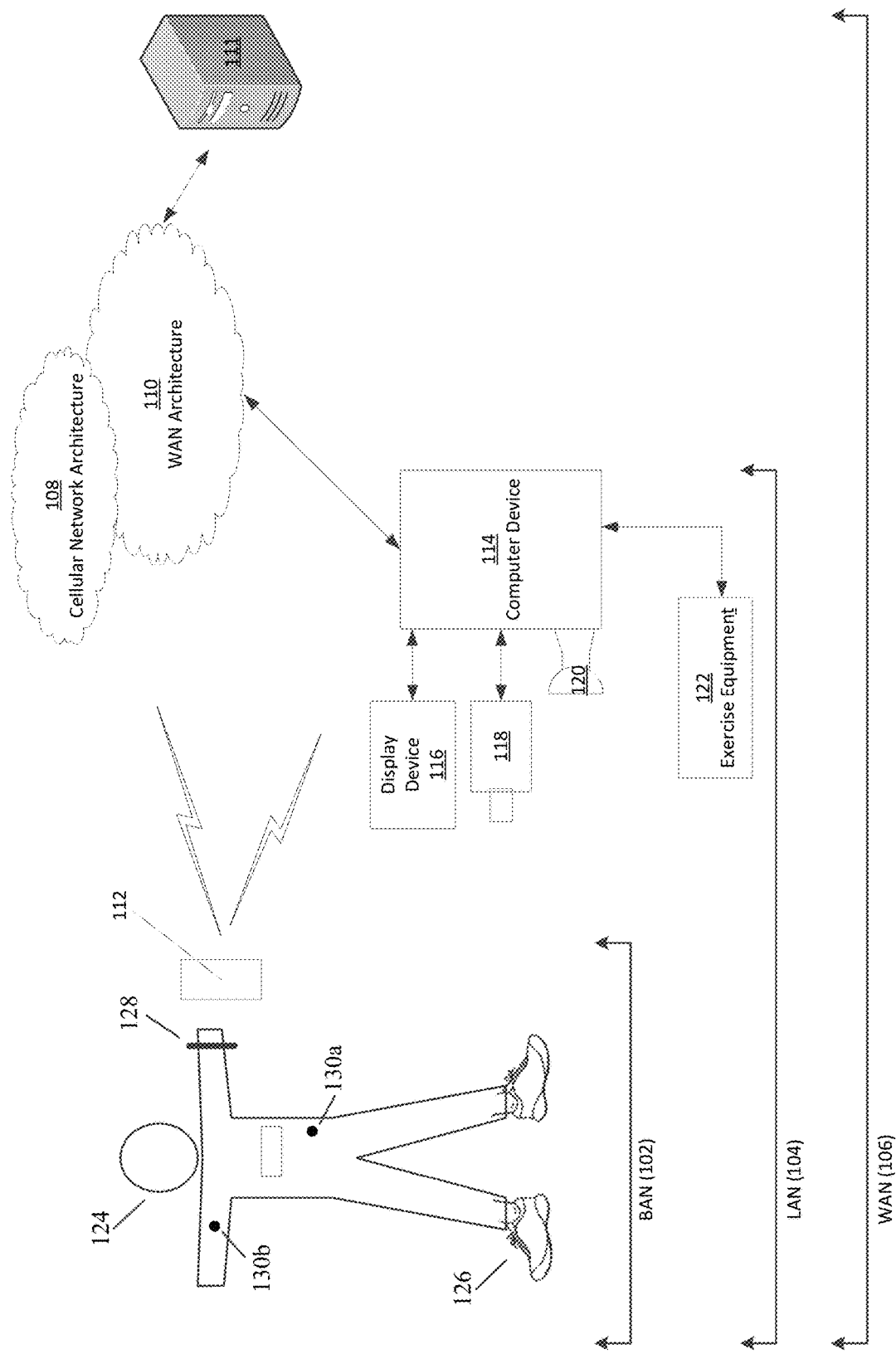
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® PlayStation, and/or a Nintendo® Wii gaming consoles. Those skilled in the art will appreciate that these are merely example devices for descriptive purposes and this disclosure is not limited to any console or computing device.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used (or be utilized) in the formation of a variety of different parameters, metrics or physiological characteristics including but not limited to: motion parameters, or motion data, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise sever 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access points permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, power balls, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such one or more of the sensors discussed above in relation to FIGS. 1-3, that may provide information utilized, either independently or in conjunction with other sensors, such as one or more sensors associated with one or more structures. For example, a backboard may comprise a first sensors configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, California or Zune® or Microsoft® Windows devices available from Microsoft of Redmond, Washington. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an-all day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
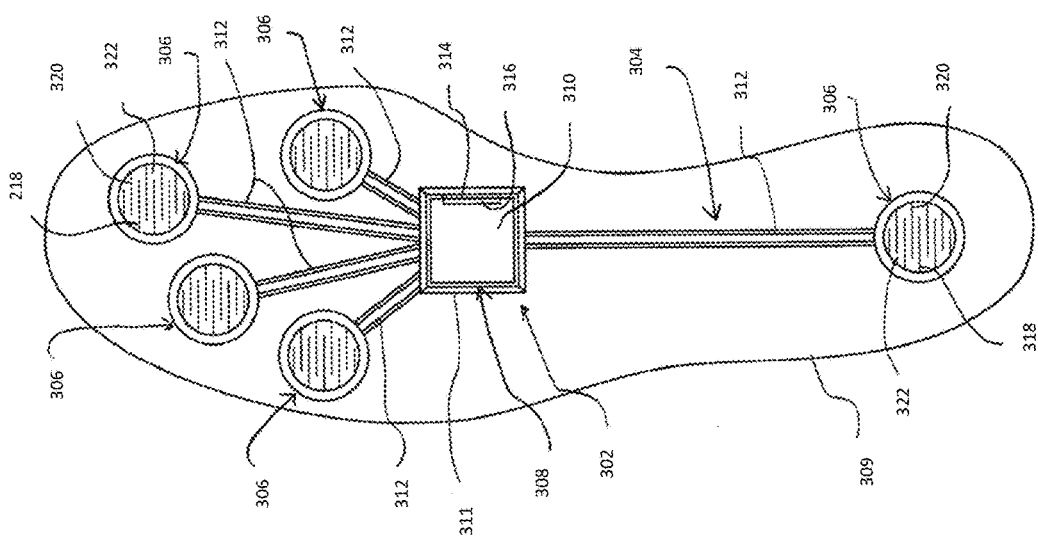
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance" may be measured, which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
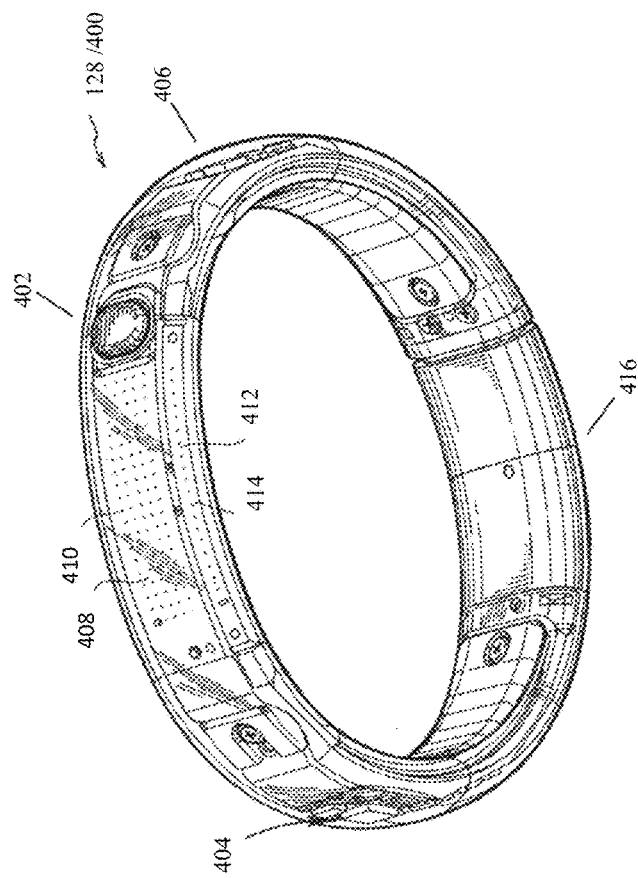
FIG. 4 shows another illustrative sensor assembly that may be worn by a user in accordance with example embodiments.

As shown in FIG. 4, device 400 (which may resemble or comprise sensory device 128 shown in FIG. 1, may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
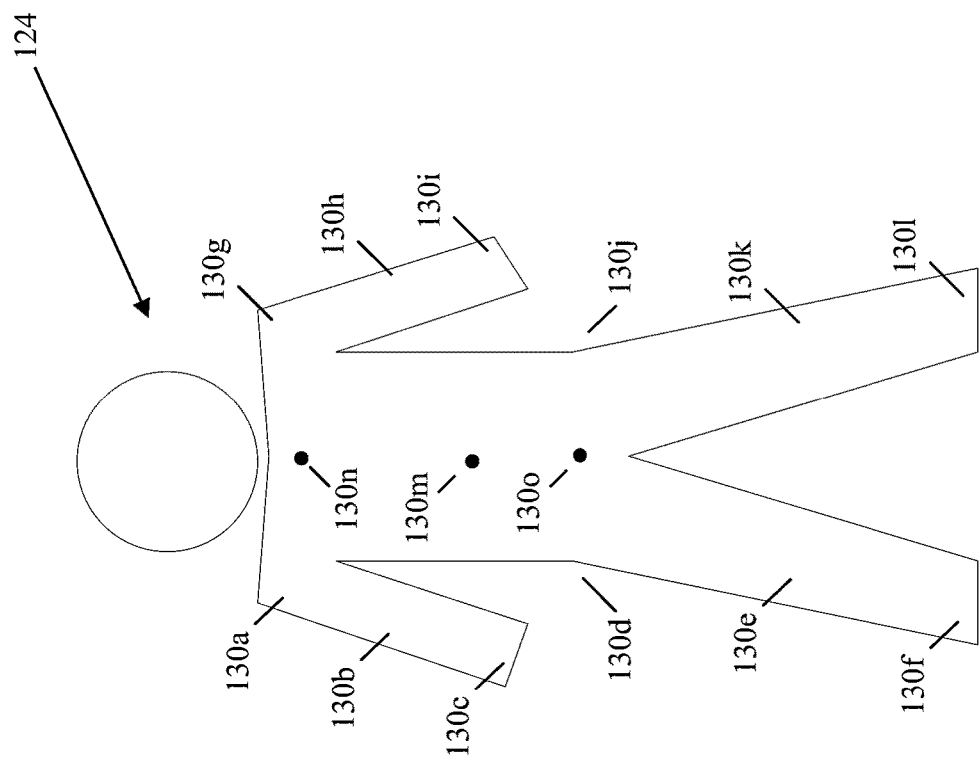
FIG. 5 shows illustrative locations for sensory input which may include physical sensors located on/in a user's clothing and/or may be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-1306o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 130n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple several sensor locations, such as sensors 130m-130o, may be utilized in determining orientation of the user 124 and/or rotational forces, such as twisting of user's 124 torso. Further, one or more locations, such as location(s), may be utilized to as a center of moment location. For example, in one embodiment, one or more of location(s) 130m-130o may serve as a point for a center of moment location of user 124. In another embodiment, one or more locations may serve as a center of moment of specific body parts or regions.

Figure 6:
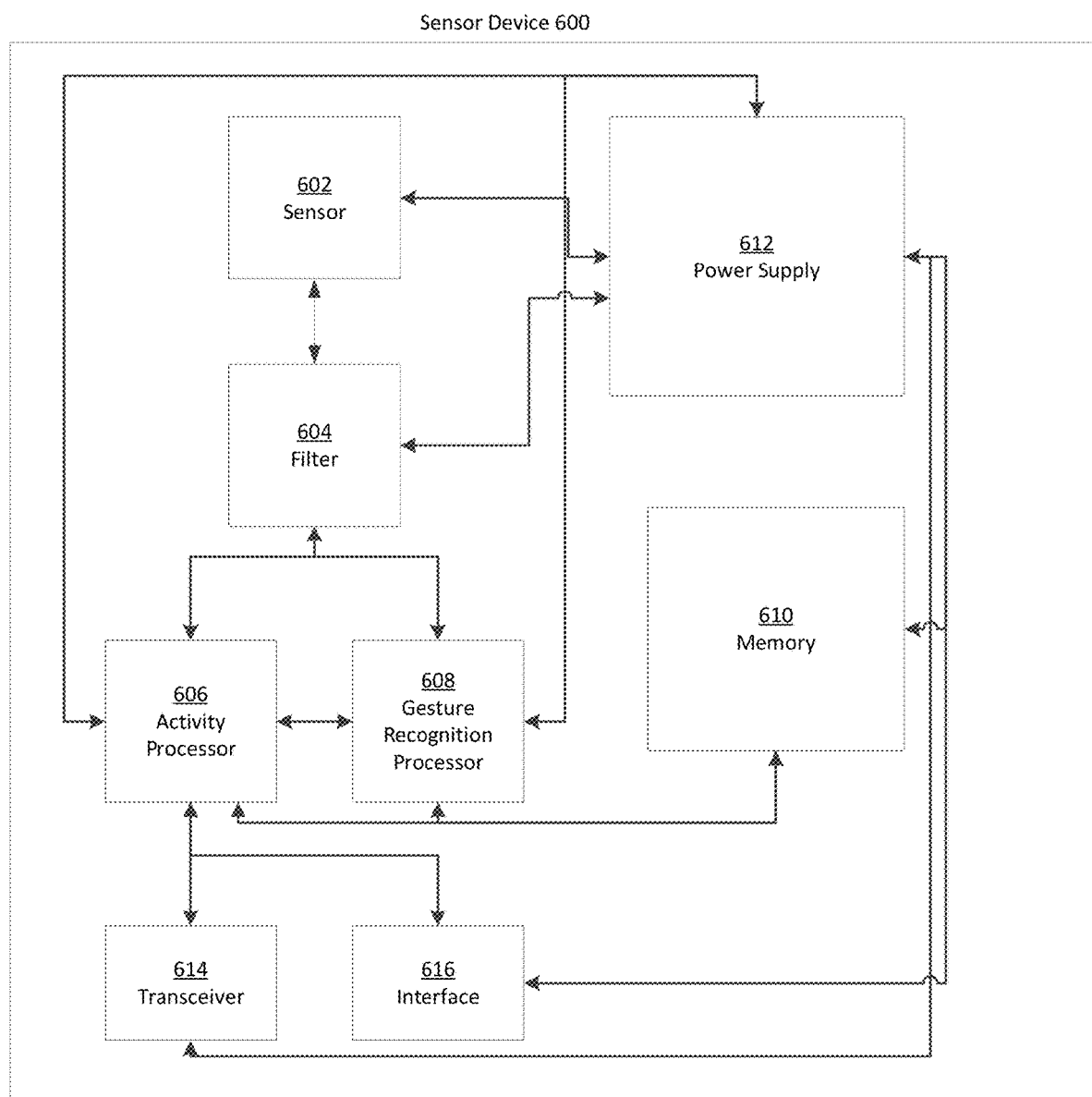
FIG. 6 is a schematic block diagram of an exemplary sensor device that may be utilized for gesture recognition.

FIG. 6 depicts a schematic block diagram of a sensor device 600 that is configured to recognize one or more gestures in accordance with certain embodiments. As shown, sensor device 600 may be embodied with (and/or in operative communication with) elements configurable to recognize one or more gestures from sensor data received by/output by the sensor device 600. In accordance with one embodiment, a recognized gesture may execute one or more processes in accordance with one or more operational modes of sensor device 600, in addition to bringing about a reduction in power consumption by one or more integral components. Illustrative sensor device 600 is shown as having a sensor 602, a filter 604, an activity processor 606, a gesture recognition processor 608, a memory 610, a power supply 612, a transceiver 614, and an interface 616. However, one of ordinary skill in the art will realize that FIG. 6 is merely one illustrative example of sensor device 600, and that sensor device 600 may be implemented using a plurality of alternative configurations, without departing from the scope of the processes and systems described herein. For example, it will be readily apparent to one of ordinary skill that activity processor 606 and gesture recognition processor 608 may be embodied as a single processor, or embodied as one or more processing cores of a single multi-core processor, among others. In other embodiments, processors 606 and 608 may be embodied using dedicated hardware, or shared hardware that may be localized (on a common motherboard, within a common server, and the like), or may be distributed (across multiple network-connected servers, and the like).

Figure 2:
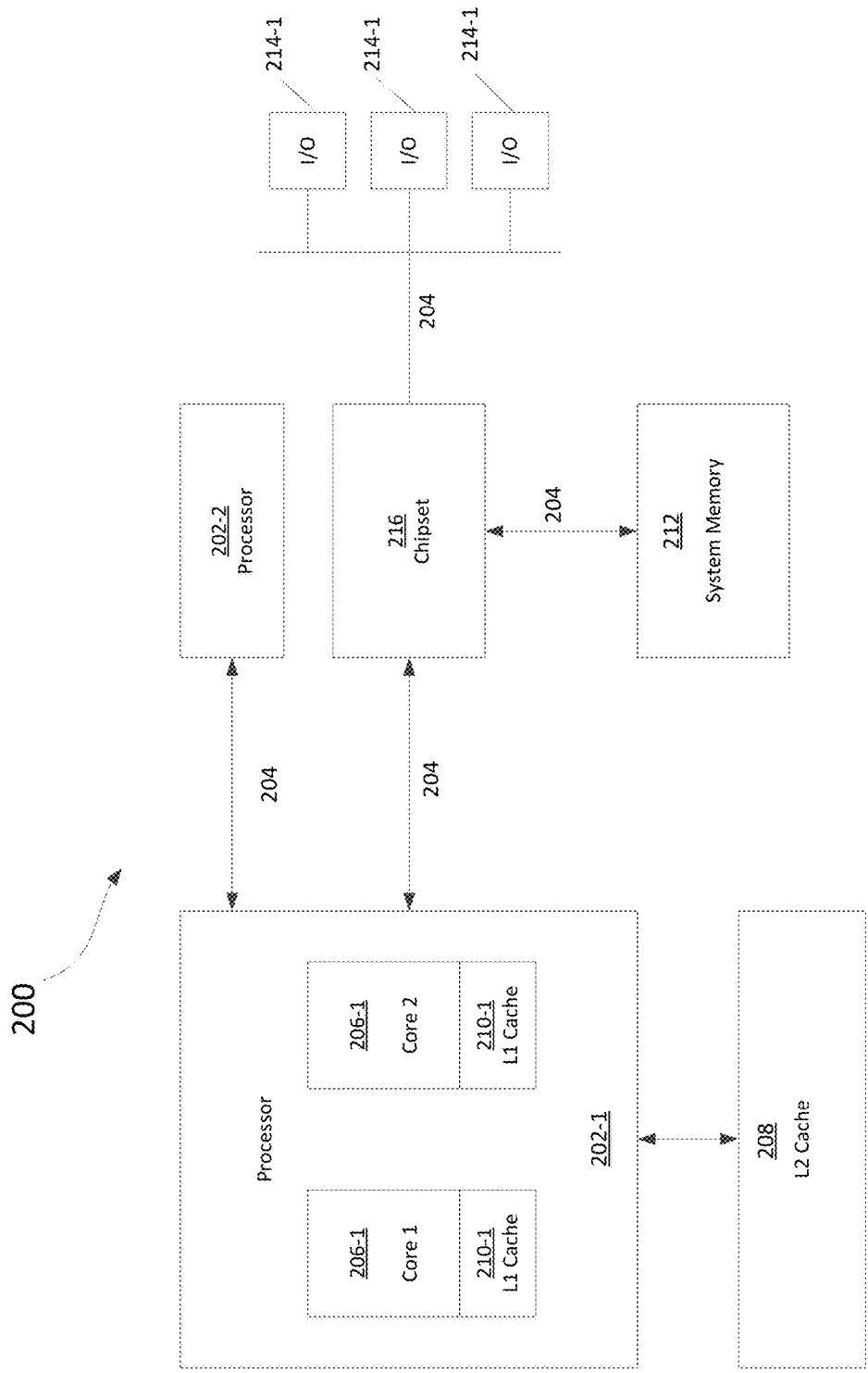
FIG. 2 illustrates an example computer device that may be part of or in communication with the system of FIG. 1.

Additionally, sensor device 600 may include one or more components of computing system 200 of FIG. 2, wherein sensor device 600 may be considered to be part of a larger computer device, or may itself be a stand-alone computer device. Accordingly, in one implementation, sensor device 600 may be configured to perform, partially or wholly, the processes of controller 404 from FIG. 4. In such an implementation, sensor device 600 may be configured to, among other things, recognize one or more gestures performed by a user of a wrist-worn device 400. In response, the wrist-worn device 400 may execute one or more processes to, among others, adjust one or more data analysis conditions or settings associated with one or more operational modes, recognize one or more activities being performed by the user, or bring about a reduction in power consumption by a wrist-worn device 400, or combinations thereof.

In one implementation, power supply 612 may comprise a battery. Alternatively, power supply 612 may be a single cell deriving power from stored chemical energy (a group of multiple such cells commonly referred to as a battery), or may be implemented using one or more of a combination of other technologies, including solar cells, capacitors, which may be configured to store electrical energy harvested from the motion of device 400 in which sensor device 600 may be positioned, a supply of electrical energy by "wireless" induction, or a wired supply of electrical energy from a power mains outlet, such as a universal serial bus (USB 1.0/1.1/2.0/3.0 and the like) outlet, and the like. It will be readily understood to one of skill that the systems and methods described herein may be suited to reducing power consumption from these, and other power supply 612 embodiments, without departing from the scope of the description.

In one implementation, sensor 602 of sensor device 600 may include on or more accelerometers, gyroscopes, location-determining devices (GPS), light sensors, temperature sensors, heart rate monitors, image-capturing sensors, microphones, moisture sensors, force sensors, compasses, angular rate sensors, and/or combinations thereof, among others. As one example embodiment comprising an accelerometer, sensor 602 may be a three-axis (x-, y-, and z-axis) accelerometer implemented as a single integrated circuit, or "chip", wherein acceleration in one or more of the three axes is detected as a change in capacitance across a silicon structure of a microelectromechanical system (MEMS) device. Accordingly, a three-axis accelerometer may be used to resolve an acceleration in any direction in three-dimensional space. In one particular embodiment, sensor 602 may include a STMicroelectronics LIS3DH 3-axis accelerometer package, and outputting a digital signal corresponding to the magnitude of acceleration in one or more of the three axes to which the accelerometer is aligned. One of ordinary skill will understand that sensor 602 may output a digital, or pulse-width modulated signal, corresponding to a magnitude of acceleration. The digital output of sensor 602, such as one incorporating an accelerometer for example, may be received as a time-varying frequency signal, wherein a frequency of the output signal corresponds to a magnitude of acceleration in one or more of the three axes to which the sensor 602 is sensitive. In alternative implementations, sensor 602 may output an analog signal as a time-varying voltage corresponding to the magnitude of acceleration in one or more of the three axes to which the sensor 602 is sensitive. Furthermore, it will be understood that sensor 602 may be a single-axis, or two-axis accelerometer, without departing from the scope of the embodiments described herein. In yet other implementations, sensor 602 may represent one or more sensors that output an analog or digital signal corresponding to the physical phenomena/input to which the sensor 602 is responsive.

Optionally, sensor device 600 may include a filter 604, wherein filter 604 may be configured to selectively remove certain frequencies of an output signal from sensor 602. In one implementation, filter 604 is an analog filter with filter characteristics of low-pass, high-pass, or band-pass, or filter 604 is a digital filter, and/or combinations thereof. The output of sensor 602 may be transmitted to filter 604, wherein, in one implementation, the output of an analog sensor 602 will be in the form of a continuous, time-varying voltage signal with changing frequency and amplitude. In one implementation, the amplitude of the voltage signal corresponds to a magnitude of acceleration, and the frequency of the output signal corresponds to the number of changes in acceleration per unit time. However, the output of sensor 602 may alternatively be a time-varying voltage signal corresponding to one or more different sensor types. Furthermore, the output of sensor 602 may be an analog or digital signal represented by, among others, an electrical current, a light signal, and a sound signal, or combinations thereof.

Filter 604 may be configured to remove those signals corresponding to frequencies outside of a range of interest for gesture recognition, and/or activity recognition by a gesture monitoring device, such as device 400. For example, filter 604 may be used to selectively remove high frequency signals over, for example, 100 Hz, which represent motion of sensor 602 at a frequency beyond human capability. In another implementation, filter 604 may be used to remove low-frequency signals from the output of sensor 602 such that signals with frequencies lower than those associated with a user gesture are not processed further by sensor device 600.

Filter 604 may be referred to as a "pre-filter", wherein filter 604 may remove one or more frequencies from a signal output of sensor 602 such that activity processor 606 does not consume electrical energy processing data that is not representative of a gesture or activity performed by the user. In this way, pre-filter 604 may reduce overall power consumption by sensor device 600 or a system of which sensor device 600 is part of.

In one implementation, the output of filter 604 is transmitted to both activity processor 606 and gesture recognition processor 608. When sensor device 600 is powered-on in a first state and electrical energy is supplied from power supply 612, both activity processor 606 and gesture recognition processor 608 may receive a continuous-time output signal from sensor 602, wherein the output signal may be filtered by filter 604 before being received by activity processor 606 and gesture recognition processor 608. In another implementation, the sensor data received by gesture recognition processor 608 is not filtered by filter 604 whereas sensor data received by activity processor 606 has been filtered by filter 604. In yet another implementation, when sensor device 600 is powered-on in a second state, activity processor 606 and gesture recognition processor 608 receive an intermittent signal from sensor 602. Those skilled in the art will also appreciate that one or more processors (e.g., processor 606 and/or 608) may analyze data obtained from a sensor other than sensor 602.

Memory 610, which may be similar to system memory 212 from FIG. 2, may be used to store computer-executable instructions for carrying out one or more processes executed by activity processor 606 and/or gesture recognition processor 608. Memory 610 may include, but is not limited to, random access memory (RAM), read only memory (ROM), and include one or more of solid-state memory, optical or magnetic storage, and/or any other medium that can be used to store electronic information. Memory 610 is depicted as a single and separate block in FIG. 6, but it will be understood that memory 610 may represent one or more memory types which may be the same, or differ from one another. Additionally, memory 610 may be omitted from sensor device 600 such that the executed instructions are stored on the same integrated circuit as one or more of activity processor 606 and gesture recognition processor 608.

Gesture recognition processor 608 may, in one implementation, have a structure similar to processor 202 from FIG. 2, such that gesture recognition processor 608 may be implemented as part of a shared integrated-circuit, or microprocessor device. In another implementation, gesture recognition processor 608 may be configured as an application-specific integrated circuit (ASIC), which may be shared with other processes, or dedicated to gesture recognition processor 608 alone. Further, it will be readily apparent to those of skill that gesture recognition processor 608 may be implemented using a variety of other configurations, such as using discrete analog and/or digital electronic components, and may be configured to execute the same processes as described herein, without departing from the spirit of the implementation depicted in FIG. 6. Similarly, activity processor 606 may be configured as an ASIC, or as a general-purpose processor 202 from FIG. 2, such that both activity processor 606 and gesture recognition processor 608 may be implemented using physically-separate hardware, or sharing part or all of their hardware.

Activity processor 606 may be configured to execute processes to recognize one or more activities being carried out by a user, and to classify the one or more activities into one or more activity categories. In one implementation, activity recognition may include quantifying steps taken by the user based upon motion data, such as by detecting arm swings peaks and bounce peaks in the motion data. The quantification may be done based entirely upon data collected from a single device worn on the user's arm, such as for example, proximate to the wrist. In one embodiment, motion data is obtained from an accelerometer. Accelerometer magnitude vectors may be obtained for a time frame and values, such as an average value from magnitude vectors for the time frame may be calculated. The average value (or any other value) may be utilized to determine whether magnitude vectors for the time frame meet an acceleration threshold to qualify for use in calculating step counts for the respective time frame. Acceleration data meeting a threshold may be placed in an analysis buffer. A search range of acceleration frequencies related to an expected activity may be established. Frequencies of the acceleration data within the search range may be analyzed in certain implementations to identify one or more peaks, such as a bounce peak and an arm swing peak. In one embodiment, a first frequency peak may be identified as an arm swing peak if it is within an estimated arm swing range and further meets an arm swing peak threshold. Similarly, a second frequency peak may be determined to be a bounce peak if it is within an estimated bounce range and further meets a bounce peak threshold.

Furthermore, systems and methods may determine whether to utilize the arm swing data, bounce data, and/or other data or portions of data to quantify steps or other motions. The number of peaks, such as arm swing peaks and/or bounce peaks may be used to determine which data to utilize. In one embodiment, systems and methods may use the number of peaks (and types of peaks) to choose a step frequency and step magnitude for quantifying steps. In still further embodiments, at least a portion of the motion data may be classified into an activity category based upon the quantification of steps.

In one embodiment, the sensor signals (such as accelerometer frequencies) and the calculations based upon sensor signals (e.g., a quantity of steps) may be utilized in the classification of an activity category, such as either walking or running, for example. In certain embodiments, if data cannot be categorized as being within a first category (e.g., walking) or group of categories (e.g., walking and running), a first method may analyze collected data. For example, in one embodiment, if detected parameters cannot be classified, then a Euclidean norm equation may be utilized for further analysis. In one embodiment, an average magnitude vector norm (square root of the sum of the squares) of obtained values may be utilized. In yet another embodiment, a different method may analyze at least a portion of the data following classification within a first category or groups of categories. In one embodiment, a step algorithm, may be utilized. Classified and unclassified data may be utilized to calculate an energy expenditure value in certain embodiments.

Exemplary systems and methods that may be implemented to recognize one or more activities are described in U.S. patent application Ser. No. 13/744,103, filed Jan. 17, 2013, the entire content of which is hereby incorporated by reference herein in its entirety for any and all non-limited purposes. In certain embodiments, activity processor 606 may be utilized in executing one or more of the processes described in the herein including those described in the '103 application.

The processes used to classify the activity of a user may compare the data received from sensor 602 to a stored data sample that is characteristic of a particular activity, wherein one or more characteristic data samples may be stored in memory 610.

Gesture recognition processor 608 may be configured to execute one or more processes to recognize, or classify, one or more gestures performed by a user, such as a user of device 400 of which sensor device 600 may be a component. In this way, a user may perform one or more gestures in order to make selections related to the operation of sensor device 600. Accordingly, a user may avoid interacting with sensor device 600 via one or more physical buttons, which may be cumbersome and/or impractical to use during physical activity.

Gesture recognition processor 608 may receive data from sensor 602, and from this received data, recognize one or more gestures based on, among others, a motion pattern of sensor device 600, a pattern of touches of sensor device 600, an orientation of sensor device 600, and a proximity of sensor device 600 to a beacon, or combinations thereof. For example, gesture recognition processor 608 may receive acceleration data from sensor 602, wherein sensor 602 is embodied as an accelerometer. In response to receipt of this acceleration data, gesture recognition processor 608 may execute one or more processes to compare the received data to a database of motion patterns. A motion pattern may be a sequence of acceleration values that are representative of a specific motion by a user. In response to finding a motion pattern corresponding to sensor data received, gesture recognition processor 608 may execute one or more processes to change and operational mode of activity processor 606 from a first operational mode to a second operational mode. An operational mode may be a group of one or more processes that generally define the manner in which sensor device 600 operates. For instance, operational modes may include, among others, a hibernation mode of activity processor 606, an activity recognition mode of activity processor 606, and a sensor selection mode of gesture recognition processor 608, or combinations thereof. Furthermore, it will be readily understood that a motion pattern may be a sequence of values corresponding to sensor types other than accelerometers. For example, a motion pattern may be a sequence of, among others: gyroscope values, force values, light intensity values, sound volume/pitch/tone values, or a location values, or combinations thereof.

For the exemplary embodiment of sensor 602 as an accelerometer, a motion pattern may be associated with, among others, a movement of a user's arm in a deliberate manner representative of a gesture. For example, a gesture may invoke the execution of one or more processes, by sensor device 600, to display a lap time to a user. The user may wear the wrist-worn device 400 and his/her left wrist, wherein wrist-worn device 400 may be positioned on his/her left wrist with a display 408 positioned on the top of the wrist. Accordingly, the "lap-time gesture" may include "flicking," or shaking of the user's left wrist through an angle of approximately 90° and back to an initial position. Gesture recognition processor 608 may recognize this flicking motion as a lap-time gesture, and in response, display a lap time to the user on display 408. An exemplary motion pattern associated with the lap-time gesture may include, among others, a first acceleration period with an associated acceleration value below a first acceleration threshold, a second acceleration period corresponding to a sudden increase in acceleration as the user begins flicking his/her wrist from an initial position, and a third acceleration period corresponding to a sudden change in acceleration as the user returns his/her wrist from an angle approximately 90° from the initial position. It will be readily apparent to those of skill that motion patterns may include many discrete "periods," or changes in sensor values associated with a gesture. Furthermore, a motion pattern may include values from multiple sensors of a same, or different types.

In order to associate data from sensor 602 with one or more motion patterns, gesture recognition processor 608 may execute one or more processes to compare absolute sensor values, or changes in sensor values, to stored sensor values associated with one or more motion patterns. Furthermore, gesture recognition processor 608 may determine that a sequence of sensor data from sensor 602 corresponds to one or more motion patterns if one or more sensor values within received sensor data are: above/below one or more threshold values, within an acceptable range of one or more stored sensor values, or equal to one or more stored sensor values, or combinations thereof.

It will be readily apparent to those of skill that motion patterns may be used to associate gestures performed by a user with many different types of processes to be executed by sensor device 600. For example, a gesture may include motion of a user's left and right hands into a "T-shape" position and holding both hands in this position for a predetermined length of time. Gesture recognition processor 608 may receive sensor data associated with this gesture, and execute one or more processes to compare the received sensor data to one or more stored motion patterns. The gesture recognition processor 608 may determine that the received sensor data corresponds to a "timeout" motion pattern.

In response, gesture recognition processor 608 may instruct activity processor 606 to execute one or more processes associated with a "timeout" operational mode. For example, the "timeout" operational mode may include reducing power consumption by activity processor 606 by decreasing a sampling rate at which activity processor 606 receives data from sensor 602. In another example, a gesture may include motion of a user's arms into a position indicative of stretching the upper body after an athletic workout. Again, gesture recognition processor 608 may receive sensor data associated with this gesture, and execute one or more processes to compare this received data to one or more stored motion patterns. The gesture recognition processor 608, upon comparison of the received sensor data to the one or more stored motion patterns, may determine that the received sensor data corresponds to a "stretching" motion pattern. In response, gesture recognition processor 608 may instruct activity processor 606 to execute one or more processes associated with a "stretching" operational mode. This "stretching" operational mode may include processes to cease activity recognition of one or more athletic activities performed prior to a stretching gesture.

In one implementation, gestures may be recognized by gesture recognition processor 608 after execution of one or more "training mode" processes by gesture recognition processor 608. During a training mode, gesture recognition processor 608 may store one or more data sets corresponding to one or more motion patterns. In particular, gesture recognition processor 608 may instruct a user to perform a "training gesture" for a predetermined number of repetitions. For each repetition, gesture recognition processor 608 may receive data from one or more sensors 602. Gesture recognition processor 608 may compare the sensor data received for each training gesture, and identify one or more characteristics that are common to multiple gestures. These common characteristics may be stored as one or more sequences of sensor value thresholds, or motion patterns.

For example, during a training mode in which a "tell time" gesture is to be analyzed, gesture recognition processor 608 may instruct a user to carry out a specific motion three times. The specific motion may include, among others, positioning the user's left arm substantially by his/her side and in a vertical orientation, moving the left arm from a position substantially by the user's side to a position substantially horizontal and pointing straight out in front of user, and bending the user's left arm at the elbow such that the user's wrist is approximately in front of the user's chin. Gesture recognition processor 608 may execute one or more processes to identify sensor data that is common to the three "tell time" training gestures carried out by the user during the training mode, and store these common characteristics as a motion pattern associated with a "tell time" gesture. Gesture recognition processor 608 may further store one or more processes to be carried out upon recognition of the "tell time" gesture, which may include displaying a current time to the user on a display 408. In this way, if the user's motion corresponds to the "tell time" gesture in the future, as determined by the gesture recognition processor 608, a current time may be displayed to the user.

In another implementation, gesture recognition processor 608 may recognize a gesture from sensor data based on a pattern of touches of sensor device 600. In one implementation, a pattern of touches may be generated by a user as a result of tapping on the exterior casing of device 400. This tapping motion may be detected by one or more sensors 602. In one embodiment, the tapping may be detected as one or more spikes in a data output from an accelerometer. In this way, gesture recognition processor 608 may associate a tapping pattern with one or more processes to be executed by activity processor 606. For example, gesture recognition processor 608 may receive sensor data from an accelerometer representative of one or more taps of the casing of device 400. In response, gesture recognition processor 608 may compare the received accelerometer data to one or more tapping patterns stored in memory 610, wherein a tapping pattern may include one or more accelerometer value thresholds. The gesture recognition processor 608 may determine that the received data from an accelerometer corresponds to one or more tapping patterns if, for example, the received sensor data contains multiple "spikes," or peaks in the acceleration data with values corresponding to those stored in the tapping patterns, and within a predetermined time period of one another. For example, gesture recognition processor 608 may determine that data received from an accelerometer corresponds to a tapping pattern if the received sensor data contains two acceleration value peaks with average values over a threshold of 2.0 g (g=acceleration due to gravity), and within 500 ms of one another.

In another implementation, a pattern of touches may be generated by a user swiping one or more capacitive sensors in operative communication with sensor device 600. In this way, a pattern of touches may be comprised of movement of one or more of a user's fingers according to a predetermined pattern across the one or more capacitive sensors.

In yet another implementation, gesture recognition processor 608 may recognize a gesture based upon an orientation of sensor device 600 within device 400. An orientation of sensor device 600 may be received from, among others, sensor 602 embodied as an accelerometer, a gyroscope, or a magnetic field sensor, or combinations thereof. In this way, gesture recognition processor 608 may receive data from sensor 602 representative of an orientation of sensor device 600, and associate this sensor data with an orientation gesture. In turn, this orientation gesture may invoke gesture recognition processor 608 to execute one or more processes to select an operational mode for activity processor 606. In one example, device 400 is positioned on a user's wrist. Device 400 may be oriented such that display 408 is positioned on top of the user's wrist. In this instance, the "top" of the user's wrist may be defined as the side of the user's wrist substantially in the same plane as the back of the user's hand. In this example, an orientation gesture may be associated with a user rotating his/her wrist, and accordingly device 400, such that display 408 faces substantially downwards. In response to recognition of this orientation gesture, gesture recognition processor 608 may execute one or more processes to, among others, increase the sampling rate of activity processor 606 in preparation for a period of vigorous activity. In another example, an orientation gesture may be associated with the orientation of a user's hands on the handlebars of a road bicycle, wherein a first grip orientation gesture may be associated with sprinting while on a road bicycle, and a second grip orientation gesture may be associated with uphill climbing on a road bicycle, among others. Furthermore, it will be readily apparent to one of ordinary skill less many more orientation gestures may be defined without departing from the spirit of the disclosure described herein.

In another embodiment, gesture recognition processor 608 may recognize a gesture associated with the proximity of sensor device 600 to a beacon. A beacon may be an electronic device, such as a transceiver, which is detectable when within a predetermined range of sensor device 600. A beacon may emit a short-range signal that includes information identifying one or more pieces of information associated with the beacon, wherein a beacon may represent, for example, the starting point of a marathon/running race, a distance marker along the length of the marathon, or in the finish point of the marathon. The signal associated with a beacon may be transmitted using a wireless technology/protocol including, among others: Wi-Fi, Bluetooth, or a cellular network, or combinations thereof. The signal emitted from a beacon may be received by transceiver 614 of sensor device 600. Upon receipt of a beacon signal, the transceiver 614 may communicate data to gesture recognition processor 608. In response, gesture recognition processor 608 may identify the received data as a proximity gesture. In this example, the identified proximity gesture may be associated with one or more processes configured to update progress times associated with a user's marathon run.

In yet another embodiment, a proximity gesture may be associated with a sensor device 600 coming into close proximity with, among others, another user, or an object. In this way, a proximity gesture may be used, for example, to execute one or more processes based on multiple individuals competing as part of a sports team, or based on a runner coming into close proximity with a starting block equipped with a beacon on a running track, and the like.

Figure 7:
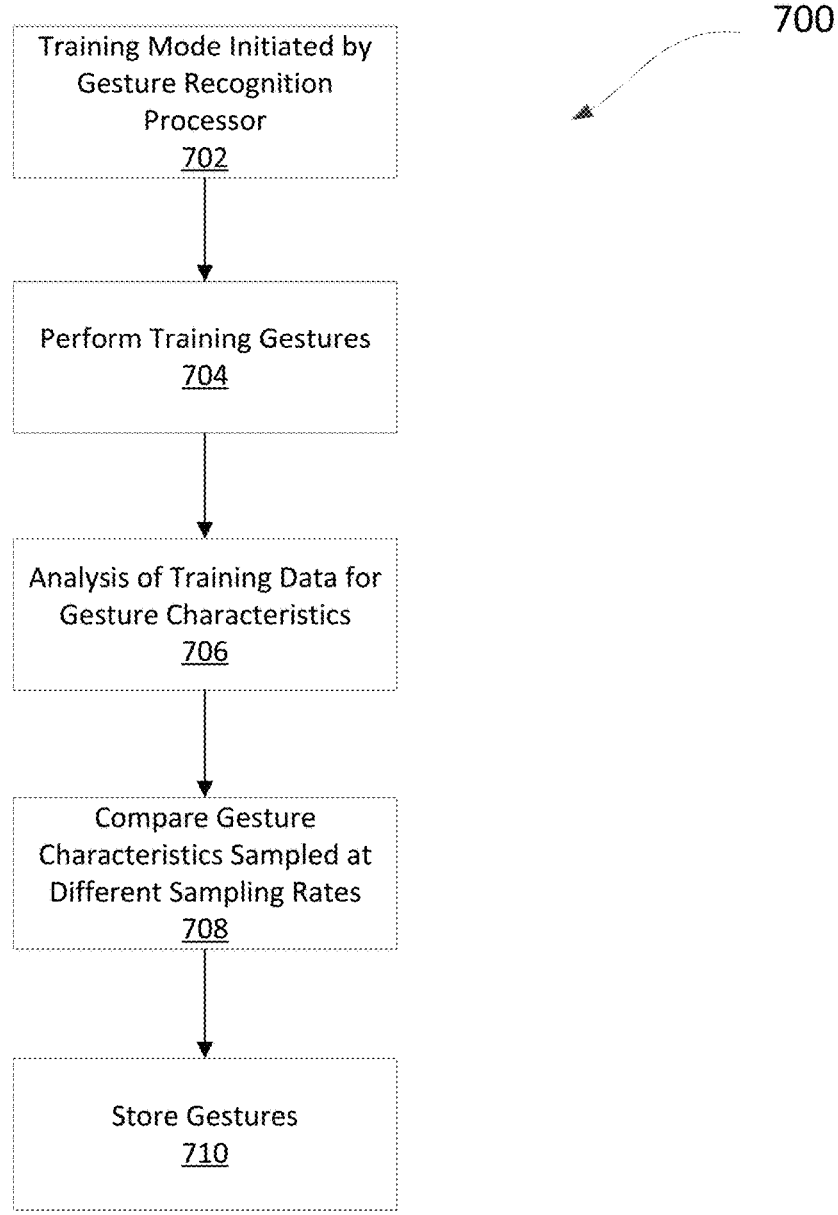
FIG. 7 is a schematic block diagram of a gesture recognition training process.

FIG. 7 is a schematic block diagram of a gesture recognition training process 700. This gesture recognition training process 700 may be executed as, among others, a "training mode" by the gesture recognition processor 608. In particular, process 700 begins at block 702, wherein a training mode is initiated by the gesture recognition processor 608. The training mode may be initiated in response to initialization of sensor device 600 for a first time, or at any time during use of sensor device 600, in order to save new gesture patterns into memory 610. Accordingly, these saved gesture patterns may be recognized by gesture recognition processor 608 during "normal" operation of device 600 wherein normal operation of device 600 may be defined as any time during which device 600 is powered-on and not executing a training process 700.

During the gesture recognition training process 700, the gesture recognition processor 608 may instruct a user to perform multiple successive repetitions of a training gesture. In one embodiment, the motions associated with a gesture may be defined by the user, while in another embodiment, the motions may be prescribed by the gesture recognition processor 608 to be performed by the user. Block 704 of process 700 includes, among others, the user performing the multiple successive repetitions of a training gesture. In one implementation, the number of successive repetitions of the training gesture may range from 1 to 10, but it will be readily apparent to those of skill that any number of repetitions of the training gesture may be employed during the training process 700.

Gesture recognition processor 608 may store one or more samples of the performed training gestures in memory 610. Characteristics common to one or more of the training gestures may be identified by the gesture recognition processor 608 at block 708 of process 700. Specifically, block 708 represents one or more comparison processes executed by gesture recognition processor 608 to identify sensor data points that characterize the performed training gestures. These characteristics may be, among others, peaks in acceleration data, or changes in gyroscope data points above a threshold value, and the like. Block 708 may also include a comparison of one or more training gestures sampled at different sampling rates. In this way, and for a given training gesture, gesture recognition processor 608 may identify a sampling rate that is below an upper sampling rate associated with activity processor 606. At this lower sampling rate, the training gesture may still be recognized as if data from sensor 602 was sampled at the upper sampling rate. Gesture recognition processor 608 may store the lower sampling rate in combination with the gesture sample. Subsequently, and upon recognition, by gesture recognition processor 608, of the gesture from sensor data received during normal operation of sensor device 600, gesture recognition processor 608 may instruct activity processor 606 to sample the data at the lower sampling rate, and thereby reduce power consumption by activity processor 606.

Block 710 represents the storage of one or more gesture samples in memory 610. Gesture recognition processor 608 may poll a database of stored gesture samples upon receipt of data from sensor 602 during normal operation of sensor device 600. A gesture sample may be stored as a sequence of data points corresponding to one or more sensor values associated with one or more sensor types. Additionally, a gesture sample may be associated with one or more processes, such that upon recognition, by gesture recognition processor 608, of a gesture from received sensor data, the gesture recognition processor 608 may instruct activity processor 606 to execute the one or more associated processes. These associated processes may include processes to transition sensor device 600 from a first operational mode into a second operational mode, among others.

Figure 8:
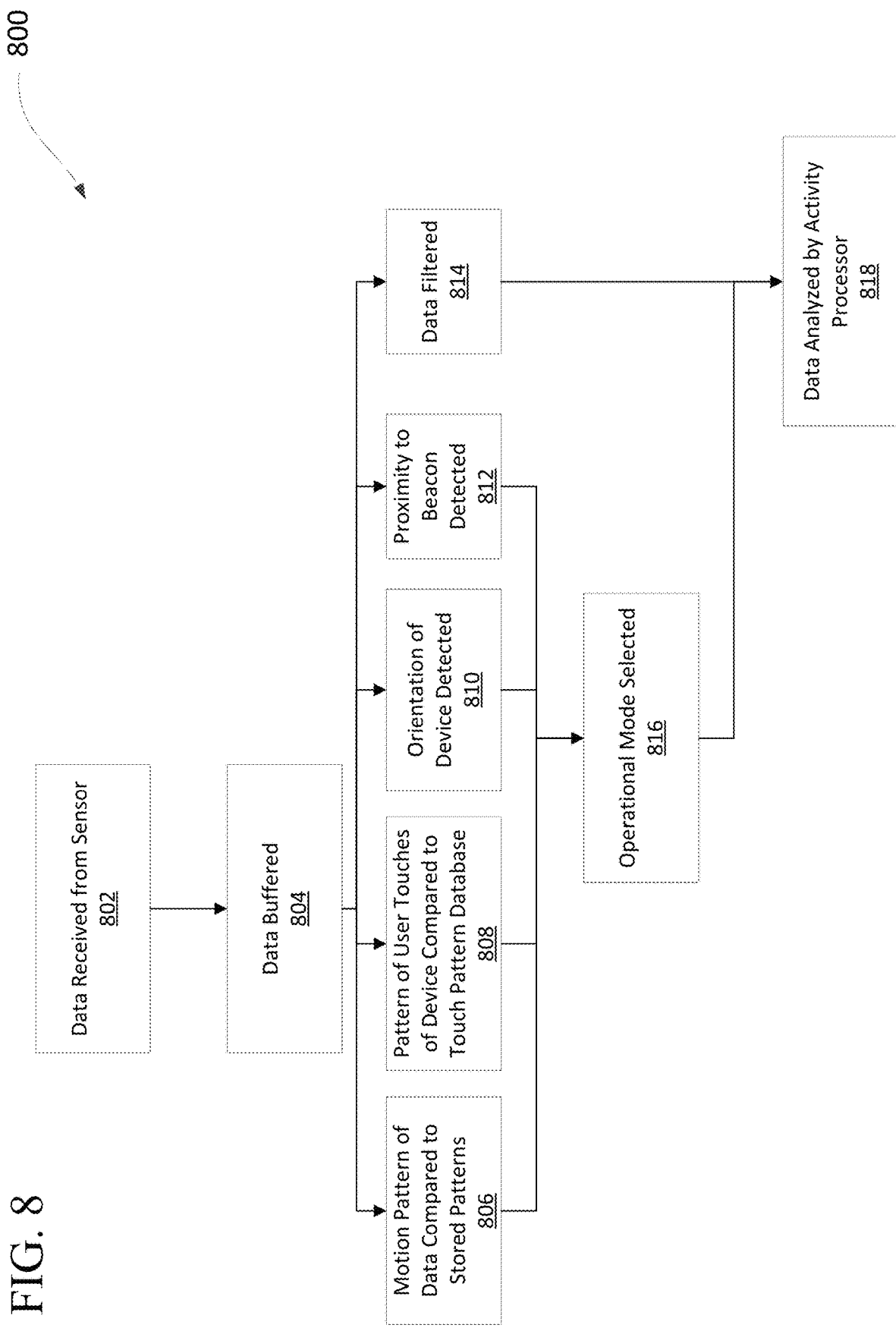
FIG. 8 is a schematic block diagram of gesture recognition process.

FIG. 8 is a schematic block diagram of a gesture recognition process 800. Gesture recognition process 800 may be, in one implementation, performed by gesture recognition processor 608. Process 800 is executed by gesture recognition processor 608 and response to a receipt of data from a sensor 602. This receipt of sensor data represented by block 802. As previously disclosed, a data output from a sensor 602 may be analog or digital. Furthermore, data output from a sensor 602 may be in the form of a data stream, such that the data output is continuous, or the data output may be intermittent. The data output from the sensor 602 may be comprised of one or more data points, wherein a data point may include, among others, an identification of the sensor type from which was generated, and one or more values associated with a reading from the sensor type.

Process 800 may include buffering of one or more data points received from a sensor 602. This is represented by block 804, wherein a buffer circuit, or one or more buffer processes, may be used to temporarily store one or more received data points. In this way, gesture recognition processor 608, or activity processor 606, may poll a buffer to analyze data received from the sensor 602.

In one implementation, gesture recognition processor 608 compares the data received from sensor 602 one or more stored motion patterns. This is represented by block 806 of process 800. In one embodiment, gesture recognition processor 608 identifies a sensor type from which data has been received. In response, gesture recognition processor 608 polls memory 610 for stored motion patterns associated with the identified sensor type. Upon response from polled memory 610 of those one or more stored motion patterns associated with the identified sensor type, gesture recognition processor 608 may iteratively search through the stored motion patterns for a sequence of sensor values that corresponds to the received data. Gesture recognition processor 608 may determine that the received data corresponds to a stored sequence of sensor values associated with a motion pattern if, among others, the received data is within a range of the stored sequence of sensor values. In another embodiment, gesture recognition processor 608 does not poll memory 610 for motion patterns associated with an identified sensor type, and instead, performs an iterative search for stored motion patterns corresponding to received sensor data.

In another implementation, gesture recognition processor 608 may execute one or more processes to compare the data received from sensor 602 to one or more stored touch patterns. This is represented by block 808 of process 800. The one or more stored touch patterns may be associated with, among others, a sequence of taps of the outer casing of device 400 of which sensor device 600 is a component. These touch patterns may be stored in a database in memory 610, such that gesture recognition processor 608 may poll this touch pattern database upon receipt of sensor data from sensor 602. In one embodiment, gesture recognition processor 608 may identify one or more peaks in the data output from sensor 602, wherein the one or more peaks in the data output may be representative of a one or more respective "taps" of sensor device 600. In response, gesture recognition processor 608 may poll memory 610 for one or more touch patterns with a one or more peaks corresponding to the received output data from sensor 602.

In another implementation, and at block 810 of process 800, gesture recognition processor 608 may recognize a gesture based on an orientation of sensor device 600. Gesture recognition processor 608 may detect an orientation of sensor device 600 based on data received from a sensor 602, wherein an orientation may be explicit from data received from a sensor 602 embodied as, among others, an accelerometer, gyroscope, or a magnetic field sensor, or combinations thereof.

In yet another implementation, gesture recognition processor 608 may recognize a gesture based on a detected proximity of sensor device 600 to a beacon. This is represented by block 812 of process 800. In one embodiment, sensor 602 may receive a signal representing a proximity of sensor device 600 to a beacon via transceiver 614.

Gesture recognition processor 608 may execute one or more processes to select an operational mode of sensor device 600, and specifically, activity processor 606. This selection of an operational mode is represented by block 816 of process 800. Furthermore, the selection of an operational mode may be in response to the recognition of a gesture, and wherein the gesture may be recognized by gesture recognition processor 608 based on the one or more processes associated with blocks 806, 808, 810, and 812. In one embodiment, activity processor 606 may execute one or more processes associated with a first operational mode upon initialization of sensor device 600. In another embodiment, a first operational mode may be communicated by gesture recognition processor 608 to activity processor 606 as a default operational mode. Upon recognition of a gesture, gesture recognition processor 608 may instruct activity processor 606 to execute one or more processes associated with a second operational mode. One of ordinary skill will recognize that an operational mode may include many different types of processes to be executed by one or more components of sensor device 600. In one example, an operational mode may include one or more processes to instruct activity processor 606 to receive data from one or more additional/alternative sensors. In this way, upon recognition of a gesture, activity processor 606 may be instructed to change the number, or type of sensors from which to receive data in order to recognize one or more activities. An operational mode may also include one or more processes to specify a sampling rate at which activity processor 606 is to sample data from sensor 602, among others. In this way, upon recognition of a gesture, by gesture recognition processor 608, activity processor 606 may be instructed to sample data at a sampling rate associated with a second operational mode. This sampling rate may be lower than an upper sampling rate possible for activity processor 606, such that a lower sampling rate may be associated with lower power consumption by activity processor 606.

Block 814 of process 800 represents one or more processes to filter data received from a sensor 602. Data may be filtered by filter 604, wherein filter 604 may act as a "pre-filter." By pre-filtering, filter 604 may allow activity processor 606 to remain in a hibernation, or low power state until received data is above a threshold value. Accordingly, filter 604 may communicate a "wake" signal to activity processor 606 upon receipt of data corresponding to, or above a threshold value.

Upon selection of an operational mode, activity processor 606 may analyze data received from sensor 602. This analysis is represented by block 818, wherein activity processor 606 may execute one or more processes to recognize one or more activities being performed by a user. Additionally, the data received by analysis processor 606 from sensor 602 may be received simultaneously to gesture recognition processor 608, as represented by the parallel processed pot from block 814 to block 818.

Figure 9:
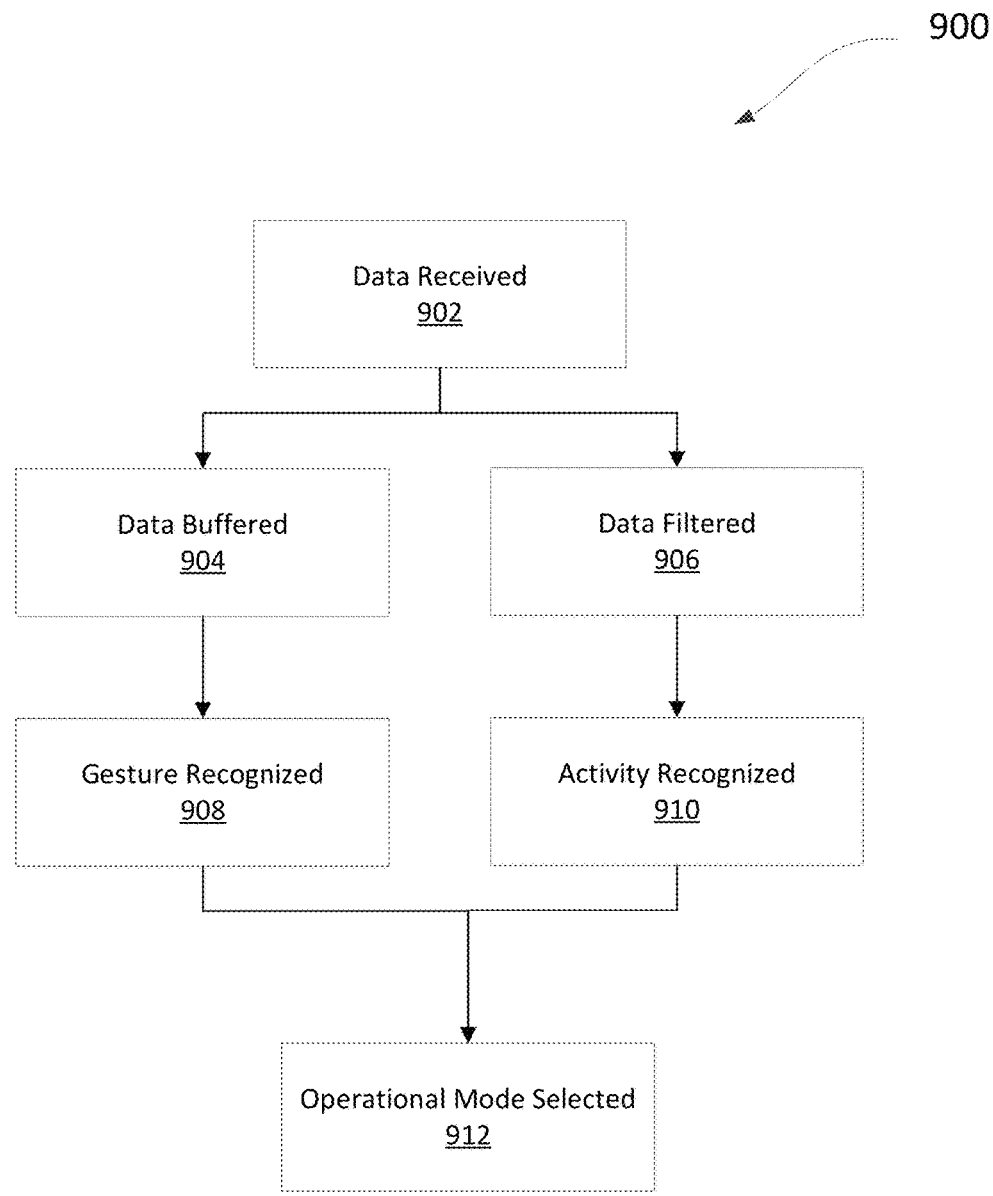
FIG. 9 is a schematic block diagram of an operational mode selection process.

FIG. 9 is a schematic block diagram of an operational mode selection process 900. Block 902 represents a receipt of data from sensor 602. In one implementation, gesture recognition processor 608 may buffer the received data, as described by block 904. Subsequently, gesture recognition processor 608 may execute one or more processes to recognize one or more gestures associated with the received data, as indicated by block 908, and as discussed in relation to process 800 from FIG. 8.

Data received at block 902 may simultaneously be communicated to activity processor 606, wherein the received data may be filtered at block 906, before being passed to activity processor 606 at block 910. Activity processor 606 may execute one or more processes to recognize one or more activities from the received sensor data at block 910, wherein this activity recognition is carried out in parallel to the gesture recognition of gesture recognition processor 608.

Block 912 of process 900 represents a selection of an operational mode, by gesture recognition processor 608. The selection of an operational mode may be based on one or more recognized gestures from block 908, and as described in relation to block 816 from process 800, but additionally considers the one or more recognized activities from block 910. In this way, a second operational mode may be selected based on one or more recognized gestures, and additionally, tailored to one or more recognized activities being performed by a user of sensor device 600.

Exemplary embodiments allow a user to quickly and easily change the operational mode in which a sensor device, such as an apparatus configured to be worn around an appendage of a user, by performing a particular gesture. This may be flicking the wrist, tapping the device, orienting the device in a particular manner, for example, or any combination thereof. In some embodiments the operation mode may be a power-saving mode, or a mode in which particular data is displayed or output. This may be particularly beneficial to a user who is participating in a physical activity where it would be difficult, dangerous, or otherwise undesirable to press a combination of buttons, or manipulate a touch-screen, for example. For example, if a user begins to run a marathon, it is advantageous that a higher sampling rate operational mode can be entered into by performing a gesture, rather than pressing a start button, or the like. Further, since operational modes can be changed by the user performing a gesture, it is not necessary to provide the sensor device with a wide-array of buttons or a complex touch-screen display. This may reduce the complexity and/or cost and/or reliability and/or durability and/or power consumption of the device.

Furthermore, in some embodiments the sensor device may recognize that a physical activity has commenced or ended. This may be recognized by a gesture and/or activity recognition. This automatic recognition may result in the operational mode being changed in response. For example, if the sensor device recognizes or determines that physical activity has ended, it may enter an operational mode in which the power consumption is reduced. This may result in improved battery life which may be particularly important for a portable or wearable device.

The sensor device 600 may include a classifying module configured to classify the captured acceleration data as one of a plurality of gestures. The sensor device 600 may also include an operational mode selection module configured to select an operational mode for the processor based on at least the classified gesture. These modules may form part of gesture recognition processor 608.

The sensor device 600 may include an activity recognition module configured to recognize an activity based on the acceleration data. This module may form part of the activity processor 606.

In any of the above aspects, the various features may be implemented in hardware, or as software modules running on one or more processors. Features of one aspect may be applied to any of the other aspects.

There may also be provided a computer program or a computer program product for carrying out any of the methods described herein, and a computer readable medium having stored thereon a program for carrying out any of the methods described herein. A computer program may be stored on a computer-readable medium, or it could, for example, be in the form of a signal such as a downloadable data signal provided from an Internet website, or it could be in any other form.

For the avoidance of doubt, the present application extends to the subject-matter described in the following numbered paragraphs (referred to as "Para" or "Paras"):

Para 1. A computer-implemented method of operating a device configured to be worn by a user and including an accelerometer, the method comprising:
(a) operating the device in a first operational mode;
(b) obtaining acceleration data representing movement of an appendage of the user using the accelerometer;
(c) classifying the acceleration data obtained in (b) as one of a plurality of gestures;
(d) entering a second operational mode based upon at least the classified gesture;
(e) obtaining acceleration data representing movement of an appendage of the user using the accelerometer;
(f) classifying the acceleration data obtained in (b) as one of a plurality of gestures.

Para 2. The computer-implemented method of Para 1, wherein the gesture is classified based on a motion pattern of the device.

Para 3. The computer-implemented method of Para 1 or 2, wherein the gesture is classified based on a pattern of touches of the device by the user.

Para 4. The computer-implemented method of Para 3, wherein the pattern of touches is a series of taps of the device by the user.

Para 5. The computer-implemented method of any of Paras 1-4, wherein the gesture is classified based on an orientation of the device.

Para 6. The computer-implemented method of any of Paras 1-5, wherein the gesture is classified based on a proximity of the device to a beacon.

Para 7. The computer-implemented method of Para 6, wherein the device is a first sensor device, and the beacon is associated with a second device on a second user.

Para 8. The computer-implemented method of Para 6 or 7, wherein the beacon is associated with a location, and the device is registered at the location based on the proximity of the device to the beacon.

Para 9. The computer-implemented method of any of Paras 1-8, further comprising:
comparing a first value of acceleration data obtained using the accelerometer against a plurality of threshold values;
determining that the first value of acceleration data corresponds to a first threshold value within the plurality the threshold values; and
wherein the classification of the acceleration data as a gesture is based upon the correspondence of the first value of acceleration data to the first threshold.

Para 10. A non-transitory computer-readable medium comprising executable instructions that when executed cause a computer device to perform the method as described in any of Paras 1 to 9.

Para 11. A unitary apparatus configured to be worn around an appendage of a user, comprising:
a sensor configured to capture acceleration data from the appendage of the user;
a processor configured to receive the captured acceleration data;
a classifying module configured to classify the captured acceleration data as one of a plurality of gestures;
an operational mode selection module configured to select an operational mode for the processor based on at least the classified gesture, wherein the processor samples data from the accelerometer based on the operational mode.

Para 12. The unitary apparatus of Para 11, wherein the operational mode selection module is configured to select a sampling rate at which data is sampled from the sensor based on the classified gesture.

Para 13. The unitary apparatus of Para 11 or 12, wherein the operational mode is a hibernation mode such that the processor uses a low level of power.

Para 14. The unitary apparatus of any of Paras 11-12, further comprising:
an activity recognition module configured to recognize an activity based on the acceleration data;
wherein the operational mode selection module is configured to select an operational mode based on at least the recognized activity and the classified gesture.

Para 15. The unitary apparatus of Paras 11-14, further comprising:
a second sensor configured to capture motion data from the user; and
wherein the processor selects to receive motion data from the second sensor data based on the classified gesture.

Para 16. The unitary apparatus of any of Paras 11-15, wherein the sensor, or second sensor, is one selected from a group comprising: an accelerometer, a gyroscope, a force sensor, a magnetic field sensor, a global positioning system sensor, and a capacitance sensor.

Para 17. The unitary apparatus of any of Paras 11-16, wherein the unitary apparatus is a wristband.

Para 18. A non-transitory computer-readable medium comprising executable instructions that when executed cause a computer device to function as a unitary apparatus as described in any of Paras 11 to 17.

Para 19. A computer-implemented method of operating a device including a sensor, the method comprising:
receiving motion data of a user from the sensor;
identifying a gesture from the received motion data;
adjusting an operational mode of the device based on the gesture identified.

Para 20. The computer-implemented method of Para 19, wherein the sensor is one selected from a group comprising: an accelerometer, a gyroscope, a force sensor, a magnetic field sensor, a global positioning system sensor, and a capacitance sensor.

Para 21. The computer-implemented method of Para 19 or 20, wherein the gesture is identified based on a motion pattern of the sensor device.

Para 22. The computer-implemented method of any of Paras 19-21, wherein the gesture is identified based on a pattern of touches of the sensor device by the user.

Para 23. The computer-implemented method of any of Paras 19-22, wherein the gesture is identified based on an orientation of the sensor device.

Para 24. A non-transitory computer-readable medium comprising executable instructions that when executed cause a computer device to perform the method as described in any of Paras 19 to 23.

What is claimed is:
1. A method comprising:
causing, by a device comprising a processor, gesture training to recognize a gesture, wherein the gesture training comprises:

sampling, at a plurality of different sampling rates, first raw sensor data associated with performance of a training gesture;

identifying, from the sampled first raw sensor data, one or more characteristics of the training gesture;

identifying, from the sampled first raw sensor data, a sampling rate, of the plurality of different sampling rates, that is lower than an upper sampling rate, of the plurality of different sampling rates, and at which the one or more characteristics of the training gesture are recognized as if sampled at the upper sampling rate; and storing the one or more characteristics of the training gesture as a gesture sample for a first gesture and storing the lower sampling rate together with the gesture sample, wherein the stored gesture sample is one of a plurality of stored gesture samples;

recognizing, from a first portion of second raw sensor data, that the device is in proximity to a beacon;

recognizing, from a second portion of the second raw sensor data and based on comparing one or more characteristics of the second portion to the plurality of stored gesture samples, the first gesture; and causing, based on the proximity to the beacon and the first gesture, the device to sample data at the lower sampling rate.

2. The method of claim 1, further comprising recognizing the first gesture further based on one or more of: a motion pattern, a pattern of touches of the device, or an orientation of the device.

3. The method of claim 2, wherein the pattern of touches comprises a series of taps of the device.

4. The method of claim 1, wherein the beacon is associated with a second device worn by a second user.

5. The method of claim 1, further comprising:
registering, based on the proximity to the beacon, the device with a location associated with the beacon.

6. The method of claim 1, further comprising:
recognizing, from a third portion of the second raw sensor data, an activity being performed; and
updating, based on the proximity to the beacon, a progress time associated with the recognized activity.

7. The method of claim 1, further comprising:
adjusting, based on recognizing a second gesture:
a quantity of sensors from which to receive additional raw sensor data, or
a type of sensor from which to receive additional raw sensor data.

8. The method of claim 1, further comprising:
receiving the first raw sensor data and the second raw sensor data from one or more sensors, wherein the one or more sensors comprise one or more of: an accelerometer, a gyroscope, a force sensor, a magnetic field sensor, a global positioning system sensor, or a capacitance sensor.

9. The method of claim 1, wherein causing the device to sample the data at the lower sampling rate causes the device to enter a hibernation mode configured to cause the processor to use a low level of power.

10. A device comprising:
a processor; and
memory storing instructions that, when executed by the processor, cause the device to:
cause gesture training to recognize a gesture by causing the device to:
sample, at a plurality of different sampling rates, first raw sensor data associated with performance of a training gesture;
identify, from the sampled first raw sensor data, one or more characteristics of the training gesture;
identify, from the sampled first raw sensor data, a sampling rate, of the plurality of different sampling rates, that is lower than an upper sampling rate, of the plurality of different sampling rates, and at which the one or more characteristics of the training gesture are recognized as if sampled at the upper sampling rate; and
store the one or more characteristics of the training gesture as a gesture sample for a first gesture and storing the lower sampling rate together with the gesture sample, wherein the stored gesture sample is one of a plurality of stored gesture samples;
recognize, from a first portion of second raw sensor data, that the device is in proximity to a beacon;
recognize, from a second portion of the second raw sensor data and based on comparing one or more characteristics of the second portion to the plurality of stored gesture samples, the first gesture; and
sample, based on the the proximity to the beacon and the first gesture, data at the lower sampling rate.

11. The device of claim 1, wherein the beacon is associated with a second device worn by a second user.

12. The device of claim 1, wherein the instructions, when executed by the processor, further cause the device to:
based on the proximity to the beacon:
register with a location associated with the beacon; or
update a progress time associated with an activity recognized from a third portion of the second raw sensor data.

13. The device of claim 1, wherein the instructions, when executed by the processor, further cause the device to:
adjust, based on recognizing a second gesture:
a quantity of sensors from which to receive additional raw sensor data, or
a type of sensor from which to receive additional raw sensor data.

14. The device of claim 1, wherein the instructions, when executed by the processor, further cause the device to:
receive the first raw sensor data and the second raw sensor data from one or more sensors, wherein the one or more sensors comprise one or more of: an accelerometer, a gyroscope, a force sensor, a magnetic field sensor, a global positioning system sensor, or a capacitance sensor.

15. The device of claim 1, wherein the instructions, when executed by the processor, cause the device to, when the data is sampled at the lower sampling rate further, enter a hibernation mode configured to cause the processor to use a low level of power.

16. A non-transitory, computer-readable medium storing instructions that, when executed by a processor of a device, cause:
causing gesture training to recognize a gesture, wherein the gesture training comprises:
sampling, at a plurality of different sampling rates, first raw sensor data associated with performance of a training gesture;
identifying, from the sampled first raw sensor data, one or more characteristics of the training gesture;
identifying, from the sampled first raw sensor data, a sampling rate, of the plurality of different sampling rates, that is lower than an upper sampling rate, of the plurality of different sampling rates, and at which the one or more characteristics of the training gesture are recognized as if sampled at the upper sampling rate; and storing the one or more characteristics of the training gesture as a gesture sample for a first gesture and storing the lower sampling rate together with the gesture sample, wherein the stored gesture sample is one of a plurality of stored gesture samples;

recognizing, from a first portion of second raw sensor data, that the device is in proximity to a beacon;

recognizing, from a second portion of the second raw sensor data and based on comparing one or more characteristics of the second portion to the plurality of stored gesture samples, the first gesture; and causing, based on recognizing that the device is in proximity to the beacon and the first gesture, the device to sample data at the lower sampling rate.

17. The non-transitory, computer-readable medium of claim 16, wherein the beacon is associated with a second device worn by a second user.

18. The non-transitory, computer-readable medium of claim 16, wherein the instructions, when executed by the processor, cause: based on the proximity to the beacon: registering the device with a location associated with the beacon; or updating a progress time associated with an activity recognized from a third portion of the second raw sensor data.

19. The non-transitory, computer-readable medium of claim 16, wherein the instructions, when executed by the processor, cause: adjusting, based on recognizing a second gesture: a quantity of sensors from which to receive additional raw sensor data, or a type of sensor from which to receive additional raw sensor data.

20. The non-transitory, computer-readable medium of claim 16, wherein the instructions, when executed by the processor, cause: when the data is sampled at the lower sampling rate, the device to enter a hibernation mode configured to cause the processor to use a low level of power.

* * * * *